(12) United States Patent
Zhong et al.

(10) Patent No.: US 12,383,766 B2
(45) Date of Patent: Aug. 12, 2025

(54) RADIATION IRRADIATION SYSTEM AND CONTROL METHOD THEREFOR

(71) Applicant: NEUBORON THERAPY SYSTEM LTD., Fujian (CN)

(72) Inventors: Wan-bing Zhong, Fujian (CN); Jiang Chen, Fujian (CN)

(73) Assignee: NEUBORON THERAPY SYSTEM LTD., Fujian (CN)

( * ) Notice: Subject to any disclaimer, the term of this patent is extended or adjusted under 35 U.S.C. 154(b) by 196 days.

(21) Appl. No.: 18/215,900

(22) Filed: Jun. 29, 2023

(65) Prior Publication Data

US 2023/0330433 A1    Oct. 19, 2023

Related U.S. Application Data

(63) Continuation of application No. PCT/CN2021/140429, filed on Dec. 22, 2021.

(30) Foreign Application Priority Data

Dec. 31, 2020  (CN) .......................... 202011637729.1

(51) Int. Cl.
*A61N 5/10* (2006.01)
(52) U.S. Cl.
CPC .......... *A61N 5/1031* (2013.01); *A61N 5/1048* (2013.01); *A61N 2005/1035* (2013.01); *A61N 2005/109* (2013.01)
(58) Field of Classification Search
CPC ...... A61N 5/10; A61N 5/1031; A61N 5/1048; A61N 2005/1035; A61N 2005/109; Y02E 30/30
See application file for complete search history.

(56) References Cited

U.S. PATENT DOCUMENTS

| 5,844,241 A | 12/1998 | Liu et al. |
|---|---|---|
| 2002/0106054 A1 | 8/2002 | Caflisch et al. |
| 2013/0253255 A1 | 9/2013 | Van Niekerk |
| 2020/0324145 A1 | 10/2020 | Piestrup et al. |

FOREIGN PATENT DOCUMENTS

| CN | 103955567 A | 7/2014 |
|---|---|---|
| CN | 104376217 A | 2/2015 |
| CN | 107290774 A | 10/2017 |
| CN | 108295384 A | 7/2018 |
| CN | 109011221 A | 12/2018 |

(Continued)

OTHER PUBLICATIONS

International Search Report of PCT/CN2021/140429, Mar. 22, 2022.

(Continued)

*Primary Examiner* — Jurie Yun
(74) *Attorney, Agent, or Firm* — Troutman Pepper Locke LLP; Tim Tingkang Xia, Esq.

(57) ABSTRACT

A radiation irradiation system and a control method therefor. On the basis of weight proportions of elements in a human body and reaction intensities the elements with a neutron and a photon, the element that has influence on simulation calculation results of the neutron and the photon in an application scenario of the radiation irradiation system is screened out, and during a simulation process, only the screened-out element is simulated, so that the calculation speed can be greatly improved, and the calculation time can be reduced.

10 Claims, 7 Drawing Sheets

(56) References Cited

FOREIGN PATENT DOCUMENTS

| | | |
|---|---|---|
| CN | 109985316 A | 7/2019 |
| CN | 110310720 A | 10/2019 |
| CN | 110310743 A | 10/2019 |
| JP | 2000507848 A | 6/2000 |
| JP | 2014026801 A | 2/2014 |
| RU | 2727576 C1 | 7/2020 |
| RU | 2736917 C1 | 11/2020 |
| TW | 202039027 A | 11/2020 |

OTHER PUBLICATIONS

Liujun Pan et al., Review of convergence acceleration methods in Monte Carlo crit-icality calculations for reactor analysis, Beijing Institute of Applied Physics and Computational Mathematics, 46, 10, 2016.

Jun-chi Guo et al., Research of the Ability of Shielding of Different Aggregate With Monte Carlo Method, Nuclear Electronics & Detection Technology, 36, 12, 2016.

A.V. Dalechina et al., Increasing the Efficiency of Modeling the Radiation Source of an Electron Accelerator in Monte Carlo Dosimetry Planning, Medical Physics, 2015, No. 2.

E. V. Bogdanova et al., Test Results of Variance Reduction Techniques Applied to the Deep Penetration Problem, ISSN 1063-7788, Physics of Atomic Nuclei, 2022, vol. 85, Suppl. 2, pp. S19-S28. © Pleiades Publishing, Ltd., 2022 Russian Text C The Author(s), 2022, published in Global Nuclear Safety,2022, vol. 45, No. 4, pp. 25-39.

Nedobukh, T. A. et al., *Foundations of Radiochemistry and Dosimetry: Teaching Methodological Guide*, Yekaterinburg: Ural University Press, 2015, p. 14.

I. S. Grigoriev et al., Physical Quantities, Moscow: Energoatomizdat, 1991, p. 966.

RADIATION IRRADIATION SYSTEM AND CONTROL METHOD THEREFOR

CROSS-REFERENCE TO RELATED PATENT APPLICATION

This application is a continuation application of International Application No. PCT/CN2021/140429, filed on Dec. 22, 2021, which claims priority to Chinese Patent Application No. 202011637729.1, filed on Dec. 31, 2020, the disclosures of which are hereby incorporated by reference.

TECHNICAL FIELD

An aspect of the invention relates to a radioactive ray irradiation system, and another aspect of the invention relates to a method for controlling a radioactive ray irradiation system.

BACKGROUND

With the development of atomics, radioactive ray therapy, such as cobalt sixty, a linear accelerator, an electron beam, or the like, has become one of the major means to treat cancers. However, traditional photon or electron therapy is restricted by physical conditions of radioactive rays themselves, and thus will also harm a large number of normal tissues on a beam path while killing tumor cells. Furthermore, owing to different levels of sensitivity of tumor cells to radioactive rays, traditional radiotherapy usually has poor treatment effect on malignant tumors (for example, glioblastoma multiforme and melanoma) with radio resistance.

In order to reduce radiation injury to normal tissues around tumors, a target therapy concept in chemotherapy is applied to radioactive ray therapy. With respect to tumor cells with high radio resistance, irradiation sources with high relative biological effectiveness (RBE), such as proton therapy, heavy particle therapy, neutron capture therapy, or the like, are also developed actively now. Here neutron capture therapy combines the abovementioned two concepts, for example boron neutron capture therapy (BNCT), provides a better cancer treatment choice than traditional radioactive rays, by specific aggregation of boron-containing drugs in tumor cells in combination with precise beam regulation and control.

In BNCT, two heavily charged particles $^4$He and $^7$Li are produced by using a characteristic of a boron ($^{10}$B)-containing drug having a high capture section for a thermal neutron, and through 10B (n, α) 7Li neutron capture and a nuclear fission reaction, and the two particles have a total range approximately equivalent to a cell size, so that radiation injury to an organism may be limited to a cell level, and when the boron-containing drug is selectively aggregated in a tumor cell, a purpose of locally killing the tumor cell may be achieved on premise of not inducing too large injury to normal tissues, in collocation with a suitable neutron radiation source.

In order to make radiation particles kill cancer cells as many as possible and reduce damage to normal cells, CT or PET image-scanning is usually carried out before a patient is treated, material information of tissues of a human body are obtained according to a scanning result, a calculation model is established according to the material information and the radiation source, a transportation process of the radiation particles in the human body is simulated, a dose distribution of the radiation particles in the human body is finally obtained, and then a scheme with an optimal dose distribution on the patient is selected as the patient's therapy scheme.

At present, a dose calculation module in a radiotherapy plan system obtains a dose distribution mainly by simulating radiation particles using Monte Carlo method. Movement processes of photons and electrons need to be simulated for a traditional radiotherapy, and movement processes of neutrons and photons need to be simulated for radioactive ray irradiation therapy. At present, the Monte Carlo method is the most accurate method for dose calculation, but it consumes a very long time for calculation, and has a large memory consumption.

At present, universal Monte Carlo programs such as MCNP and Geant 4 are most often used for radiotherapy calculation, here, MCNP is initially used for reactor design and calculation, Geant 4 is initially used for high-energy physical calculation. These programs do not consider physical scenes of radiotherapy at the beginning of their designs, and thus do not perform special optimization with respect to the field of radiotherapy calculation. Formulation of a radiotherapy plan usually needs to be completed within a specified time, for example, the radioactive ray irradiation therapy requires the radiotherapy plan system to give a therapy scheme within one hour, here, a dose calculation process occupies most of the time formulated by the radiotherapy plan. Therefore, a dose calculation method needs to be optimized to reduce the time formulated by the radiotherapy plan.

SUMMARY

In order to overcome defects of the related art, a first aspect of the invention provides a radioactive ray irradiation system, including a beam irradiation device, a treatment plan module and a control module. The beam irradiation device generates a treatment beam and irradiates the treatment beam to an irradiated body, to form an irradiated site. The treatment plan module performs dose simulation and calculation according to parameters of the treatment beam and medical imaging data of the irradiated site and generates a treatment plan, screens elements with influence on simulation and calculation results of neutrons and photons in application scenes of the radioactive ray irradiation system by considering weight proportions of a plurality of elements in a human body and intensities of the plurality of elements reacting with the neutrons and the photons, so that only the screened elements are simulated during simulation. The control module controls irradiation of the beam irradiation device according to the treatment plan.

In other embodiments, the elements screened by the treatment plan module may be selected from one or more of H, He, Li, Be, B, C, N, O, F, Na, Mg, Al, Si, P, S, Cl, Ar, K and Ca.

More specifically, the elements screened by the treatment plan module may be H, He, Li, Be, B, C, N, O, F, Na, Mg, Al, Si, P, S, Cl, Ar, K and Ca.

In another embodiment, the treatment plan module may remove databases corresponding to other temperatures except 294 K and 0 K from a neutron cross-section database corresponding to each of the elements.

Preferably, the radioactive ray irradiation system may be a neutron capture therapy system, and the beam irradiation device includes a neutron generation device, a beam shaping body and a treatment table. The neutron generation device includes an accelerator and a target, the accelerator accelerates charged particles to generate a charged particle line which acts with the target to generate a neutron line. The beam shaping body is capable of adjusting the neutron line generated by the neutron generation device to have a preset beam quality, and the neutron line generated by the neutron generation device is irradiated to the irradiated body on the treatment table through the beam shaping body.

A second aspect of the invention provides a method for controlling a radioactive ray irradiation system, here, the beam irradiation system includes a beam irradiation device, a treatment plan module and a control module. The beam irradiation device generates a treatment beam and irradiates the treatment beam to an irradiated body, to form an irradiated site. The treatment plan module performs dose simulation and calculation according to parameters of the treatment beam and medical imaging data of the irradiated site and generates a treatment plan. The control module controls irradiation of the beam irradiation device according to the treatment plan. The method for controlling the radioactive ray irradiation system includes the following operations. Elements with influence on simulation and calculation results of neutrons and photons in application scenes of the radioactive ray irradiation system are screened by considering weight proportions of a plurality of elements in a human body and intensities of the plurality of elements reacting with the neutrons and the photons, so that only the screened elements are simulated during simulation.

In other embodiments, the elements screened by the treatment plan module may be selected from one or more of H, He, Li, Be, B, C, N, O, F, Na, Mg, Al, Si, P, S, Cl, Ar, K and Ca.

More specifically, the elements screened by the treatment plan module may be H, He, Li, Be, B, C, N, O, F, Na, Mg, Al, Si, P, S, Cl, Ar, K and Ca.

In another embodiment, the method for controlling the radioactive ray irradiation system may further include the following operations. The treatment plan module removes databases corresponding to other temperatures except 294 K and 0 K from a neutron cross-section database corresponding to each of the elements.

Preferably, the radioactive ray irradiation system may be a neutron capture therapy system, and the beam irradiation device includes a neutron generation device, a beam shaping body and a treatment table. The neutron generation device includes an accelerator and a target, the accelerator accelerates charged particles to generate a charged particle line which acts with the target to generate a neutron line. The beam shaping body is capable of adjusting the neutron line generated by the neutron generation device to have a preset beam quality, and the neutron line generated by the neutron generation device is irradiated to the irradiated body on the treatment table through the beam shaping body.

According to the radioactive ray irradiation system and the method for controlling the radioactive ray irradiation system recited by the embodiments of the invention, elements with influence on simulation and calculation results of neutrons and photons in application scenes of the radioactive ray irradiation system are screened by considering weight proportions of a plurality of elements in a human body and intensities of the plurality of elements reacting with the neutrons and the photons, so that only the screened elements are simulated during simulation. Therefore, calculation speed of the treatment plan module may be greatly increased, and calculation time is reduced.

A third aspect of the invention provides a radioactive ray irradiation system, including a beam irradiation device, a treatment plan module and a control module. The beam irradiation device generates a treatment beam and irradiates the treatment beam to an irradiated body, to form an irradiated site. The treatment plan module performs dose simulation and calculation according to parameters of the treatment beam and medical imaging data of the irradiated site and generates a treatment plan, here, simulation tasks of different source particles are allocated to different processes or threads, and summarization is performed after a calculation task of each of the processes or threads is completed, to obtain a final calculation result. The control module controls irradiation of the beam irradiation device according to the treatment plan.

Preferably, the radioactive ray irradiation system may be a neutron capture therapy system, and the beam irradiation device includes a neutron generation device, a beam shaping body and a treatment table. The neutron generation device includes an accelerator and a target, the accelerator accelerates charged particles to generate a charged particle line which acts with the target to generate a neutron line. The beam shaping body is capable of adjusting the neutron line generated by the neutron generation device to have a preset beam quality, and the neutron line generated by the neutron generation device is irradiated to the irradiated body on the treatment table through the beam shaping body.

In an embodiment, the particles may be simulated by process parallelism and thread parallelism of a central processing unit (CPU) and graphic processing unit (GPU) acceleration, each of the process parallelism and the thread parallelism implements parallel computation by a multi-core CPU, and a calculation process of the process parallelism and thread parallelism of the CPU is as follows. Firstly, the system obtains a number of processes or threads to obtain a numerical value n; then, the system equally divides particles required to be simulated into n parts; next, each of the threads or processes separately simulates and counts each part of the particles; and finally, the system performs counting on the count obtained by each of the processes or threads to obtain a final dose.

In an embodiment, the GPU acceleration may be implemented by parallel computation of a plurality of processors of GPU, and a simulation and computation process of the GPU acceleration is as follows. Firstly, the system transmits a random number, cross-section data, or the like from a CPU memory to a GPU video memory, and then each of the plurality of processors of the GPU simulates, calculates and counts a single particle, and counts a counting result into a global count; next, the system determines whether there are particles which are still not simulated, transmits the counting result from the GPU memory to the CPU memory in response to there being no particles which are still not simulated, or returns to the previous operation in response to there being particles which are still not simulated, to continue to simulate and count the particles which are still not simulated, until simulation of all the particles are completed.

A fourth aspect of the invention provides a method for controlling a radioactive ray irradiation system, here, the beam irradiation system includes a beam irradiation device, a treatment plan module and a control module. The beam irradiation device generates a treatment beam and irradiates the treatment beam to an irradiated body, to form an irradiated site. The treatment plan module performs dose simulation and calculation according to parameters of the treatment beam and medical imaging data of the irradiated site and generates a treatment plan. The control module controls irradiation of the beam irradiation device according to the treatment plan. The method for controlling the radioactive ray irradiation system includes the following operations. Simulation tasks of different source particles are allocated to different processes or threads, and summarization is performed after a calculation task of each of the processes or threads is completed, to obtain a final calculation result.

In an embodiment, the particles may be simulated by process parallelism and thread parallelism of CPU and GPU acceleration.

Preferably, each of the process parallelism and the thread parallelism may implement parallel computation by a multicore CPU.

In an embodiment, a calculation process of the process parallelism and thread parallelism of the CPU may be as follows. Firstly, the system obtains a number of processes or threads to obtain a numerical value n; then, the system equally divides particles required to be simulated into n parts; next, each of the threads or processes separately simulates and counts each part of the particles; and finally, the system performs counting on the count obtained by each of the processes or threads to obtain a final dose.

Preferably, the GPU acceleration may be implemented by parallel computation of a plurality of processors of GPU.

A simulation and computation process of the GPU acceleration may be as follows. Firstly, the system transmits a random number, cross-section data, or the like from a CPU memory to a GPU video memory, and then each of the plurality of processors of the GPU simulates, calculates and counts a single particle, and counts a counting result into a global count; next, the system determines whether there are particles which are still not simulated, transmits the counting result from the GPU memory to the CPU memory in response to there being no particles which are still not simulated, or returns to the previous operation in response to there being particles which are still not simulated, to continue to simulate and count the particles which are still not simulated, until simulation of all the particles are completed.

According to the radioactive ray irradiation system and the method for controlling the radioactive ray irradiation system recited by the embodiments of the invention, simulation tasks of different source particles are allocated to different processes or threads, and summarization is performed after a calculation task of each of the processes or threads is completed, to obtain a final calculation result. Therefore, calculation speed may be greatly increased, and calculation time is reduced.

A fifth aspect of the invention provides a radioactive ray irradiation system, including a beam irradiation device, a treatment plan module and a control module. The beam irradiation device generates a treatment beam and irradiates the treatment beam to an irradiated body, to form an irradiated site. The treatment plan module performs dose simulation and calculation according to parameters of the treatment beam and medical imaging data of the irradiated site and generates a treatment plan, here, simulation of a photon is stopped in response to a semi-absorption thickness of the photon being less than or equal to a first preset value. The control module controls irradiation of the beam irradiation device according to the treatment plan.

Preferably, the radioactive ray irradiation system may be a neutron capture therapy system, and the beam irradiation device includes a neutron generation device, a beam shaping body and a treatment table. The neutron generation device includes an accelerator and a target, the accelerator accelerates charged particles to generate a charged particle line which acts with the target to generate a neutron line. The beam shaping body is capable of adjusting the neutron line generated by the neutron generation device to have a preset beam quality, and the neutron line generated by the neutron generation device is irradiated to the irradiated body on the treatment table through the beam shaping body.

In an embodiment, the treatment plan module may calculate the semi-absorption thickness t of the photon by a formula (1-1):

$$t = \frac{\ln 2}{\mu} \approx \frac{0.693}{\mu} \quad (1-1)$$

here μ is a linear attenuation factor of the photon which is determined by a material passed by the photon and photon energy.

Here, the first preset value may be a cell size, preferably, the first preset value may be 0.2 mm, and when photon energy is less than or equal to a second preset value, the semi-absorption thickness of the photon corresponding to the photon energy is less than or equal to the first preset value, here, the second preset value is 10 KeV.

A sixth aspect of the invention provides a method for controlling a radioactive ray irradiation system, here, the beam irradiation system includes a beam irradiation device, a treatment plan module and a control module. The beam irradiation device generates a treatment beam and irradiates the treatment beam to an irradiated body, to form an irradiated site. The treatment plan module performs dose simulation and calculation according to parameters of the treatment beam and medical imaging data of the irradiated site and generates a treatment plan. The control module controls irradiation of the beam irradiation device according to the treatment plan. The method for controlling the radioactive ray irradiation system includes the following operations. Simulation of a photon is stopped in response to a semi-absorption thickness of the photon being less than or equal to a first preset value.

In an embodiment, the treatment plan module may calculate the semi-absorption thickness t of the photon by a formula (1-1):

$$t = \frac{\ln 2}{\mu} \approx \frac{0.693}{\mu} \quad (1-1)$$

here μ is a linear attenuation factor of the photon which is determined by a material passed by the photon and photon energy.

Here, the first preset value may be a cell size.

Preferably, the first preset value may be 0.2 mm.

When photon energy is less than or equal to a second preset value, the semi-absorption thickness of the photon corresponding to the photon energy is less than or equal to the first preset value.

Preferably, the second preset value may be 10 KeV.

According to the radioactive ray irradiation system and the method for controlling the radioactive ray irradiation system recited by the embodiments of the invention, simulation of a photon is stopped in response to a semi-absorption thickness of the photon being less than or equal to a first preset value. Therefore, calculation time may be reduced on premise of ensuring calculation accuracy.

A seventh aspect of the invention provides a radioactive ray irradiation system, including a beam irradiation device, a treatment plan module and a control module. The beam irradiation device generates a treatment beam and irradiates the treatment beam to an irradiated body, to form an irradiated site. The treatment plan module performs dose simulation and calculation according to parameters of the treatment beam and medical imaging data of the irradiated site and generates a treatment plan, here, the treatment plan module simulates particles by using variance reduction. The control module controls irradiation of the beam irradiation device according to the treatment plan.

Further, the variance reduction may include implicit capture, a weight window game and betting for split. The radioactive ray irradiation system may be a neutron capture therapy system, and the beam irradiation device includes a neutron generation device, a beam shaping body and a treatment table. The neutron generation device includes an accelerator and a target, the accelerator accelerates charged particles to generate a charged particle line which acts with the target to generate a neutron line. The beam shaping body is capable of adjusting the neutron line generated by the neutron generation device to have a preset beam quality, and the neutron line generated by the neutron generation device is irradiated to the irradiated body on the treatment table through the beam shaping body.

An eighth aspect of the invention provides a method for controlling a radioactive ray irradiation system, here, the beam irradiation system includes a beam irradiation device, a treatment plan module and a control module. The beam irradiation device generates a treatment beam and irradiates the treatment beam to an irradiated body, to form an irradiated site. The treatment plan module performs dose simulation and calculation according to parameters of the treatment beam and medical imaging data of the irradiated site and generates a treatment plan. The control module controls irradiation of the beam irradiation device according to the treatment plan. The method for controlling the radioactive ray irradiation system includes the following operations. The treatment plan module simulates particles by using variance reduction.

Further, the variance reduction may include implicit capture, a weight window game and betting for split. The operation of simulating the particles by using the variance reduction may include the following operations S1 to S9. In operation S1, a source particle is obtained. In operation S2, it is determined whether the particle collides in a grid element, and operations S3 and S4 are sequentially executed in case of collision, otherwise, operations S5 and S6 are sequentially executed. In operation S3, the implicit capture is performed. In operation S4, it is determined whether a weight is lower than a weight window, and operation S7 is executed in response to the weight being lower than the weight window, otherwise, the process returns to operation S2. In operation S5, the betting for split is performed. In operation S6, it is determining whether betting is performed, and operation S7 is executed in response to performing the betting, otherwise, the process returns to operation S2. In operation S7, it is determined whether there is dead betting, and operation S8 is executed in response to there being dead betting, otherwise, operation S9 is executed and then the process returns to operation S2. In operation S8, it is determined whether processing of the particles is completed, and the process ends in response to processing of the particles being completed, otherwise, the process returns to operation S1. In operation S9, the weight is divided by a probability of the dead betting.

Further, the betting for split may include the following operations S1 to S9. In operation S1, mesh space importance of each mesh is calculated and recorded. In operation S2, particles are obtained. In operation S3, weight window inspection and operation are performed on the particle. In operation S4, mesh space importance $I_n$ and $I_{n+1}$ before and after the particle spans a boundary of the mesh are calculated. In operation S5, comparison is performed to determine whether $I_n$ and $I_{n+1}$, and operation S6 is executed and then the process returns to operation S3 in response to $I_n$ being not greater than $I_{n+1}$, otherwise, operation S7 is executed. In operation S6, the particle is split and weight of the particle is reduced. In operation S7, it is determined whether there is dead betting for the particle, and operation S9 is executed in response to determining that there is dead betting for the particle, otherwise, operation S8 is executed and then the process returns to operation S3. In operation S8, the weight of the particle is increased. In operation S9, it is determined whether simulation of the particles is completed, and the process returns to operation S2 in response to determining that simulation of the particles is not completed, otherwise, the process ends.

Further, the implicit capture may include the following operations S1 to S7. In operation S1, particles are obtained. In operation S2, it is determined whether the particle collides in a grid element, and operation S3 is executed in case of collision, otherwise, the process returns to operation S1. In operation S3, a weight is multiplied with a probability of occurrence of scattering. In operation S4, it is determined whether the weight of the particle is less than a lowest weight, and operation S5 is executed in response to the weight being less than the lowest weight, otherwise, the process returns to operation S2. In operation S5, it is determined whether there is dead betting for the particle, and operation S7 is executed in response to there being dead betting for the particle, otherwise, operation S6 is executed and then the process returns to operation S2. In operation S6, the weight is divided by a probability of the dead betting. In operation S7, it is determined whether simulation of the particles is completed, and the process returns to operation S1 in response to determining that simulation of the particles is not completed, otherwise, the process ends.

Further, the weight window game may include the following operations S1 to S6. In operation S1, movement of the particles is simulated. In operation S2, it is determined whether the weight of the particle falls within a range of a weight window, and the process returns to operation S1 in response to the weight of the particle falling within the range of the weight window, otherwise, operation S3 is executed. In operation S3, it is determined whether the weight is greater than the weight window, operation S4 is executed and then the process returns to operation S1 in response to the weight being greater than the weight window, otherwise, operation S5 is executed. In operation S4, the particle is split and the weight is reduced. In operation S5, it is determined whether there is dead betting, and the process ends in response to there being dead betting, otherwise, operation S6 is executed and then the process returns to operation S1. In operation S6, the weight of the particle is increased.

In an embodiment, the mesh space importance may be obtained by solving an accompanying transportation equation which has a form as follows:

$$-\frac{1}{v}\frac{\partial \phi^*(r, E, \Omega, t)}{\partial t} - \Omega \cdot \nabla \phi^*(r, E, \Omega, t) + \Sigma_t(r, E)\phi^*(r, E, \Omega, t) =$$

$$S^*(r, E, \Omega, t) + \int\int \Sigma_s(r, E \to E', \Omega \to \Omega')\phi^*(r, E', \Omega', t)d\Omega', dEdE'$$

here φ* is an accompanying flux, S* is an accompanying source, v is a movement velocity of the particle, Ω is a movement direction of the particle, $\Sigma_t$ is a reaction cross-section of the particle colliding with a substance, $\Sigma_s$ is a scattering cross-section, r is position of the particle, E is energy of the particle, and t is time.

More specifically, the particle may move from a mesh with the mesh space importance of $I_n$ to a mesh with the mesh space importance of $I_{n+1}$, and when $I_{n+1} > I_n$, $m = I_{n+1}/I_n$ is set, the particle is split into m particles, weight of each of the particles is reduced to 1/m of an original weight; when $I_{n+1} < I_n$, a betting skill is performed on the particle, $P = I_{n+1}/I_n$ is set, a random number x is sampled between 0 and 1, and when x is less than P, the particle is survive and the weight is multiplied with 1/P, otherwise, there is dead betting for the particle, and simulation of the particle is terminated.

In other embodiments, the weight of the particle may have an upper limit of 10 and a lower limit of 0.25, and when the weight w of the particle is greater than 10, an integer part of w is set to be w1, a decimal part of w is set to be w2, a random number x is sampled between 0 and 1, w=w1+1 is set when x is less than w2, and w=w1 is set when x is greater than w2. Then, a particle is split into w particles for simulation, until weight of each of the particles is reduced to 1.

According to the radioactive ray irradiation system and the method for controlling the radioactive ray irradiation system recited by the embodiments of the invention, particles are simulated by using variance reduction. Therefore, calculation time may be reduced on premise of ensuring calculation accuracy.

A ninth aspect of the invention provides a radioactive ray irradiation system, including a beam irradiation device, a treatment plan module and a control module. The beam irradiation device generates a treatment beam and irradiating the treatment beam to an irradiated body, to form an irradiated site. The treatment plan module performs dose simulation and calculation according to parameters of the treatment beam and medical imaging data of the irradiated site and generates a treatment plan, here, the treatment plan module performs simulation and calculation by using non-uniform meshes. The control module controls irradiation of the beam irradiation device according to the treatment plan.

Further, a size of a mesh of an important area may be set by the treatment plan module to be less than a size of a mesh of a non-important area.

Further, a size of a mesh of an area where a tumor is located may be set by the treatment plan module to be less than or equal to 0.4 mm.

Further, a size of a mesh of an area where each of blood, air and bone is located may be set by the treatment plan module to be greater than or equal to 1.6 mm.

Further, a size of a mesh of an area where a normal muscle is located may be set by the treatment plan module to be greater than 0.8 mm and less than 1.6 mm.

Preferably, the radioactive ray irradiation system may be a neutron capture therapy system, and the beam irradiation device includes a neutron generation device, a beam shaping body and a treatment table. The neutron generation device includes an accelerator and a target, the accelerator accelerates charged particles to generate a charged particle line which acts with the target to generate a neutron line. The beam shaping body is capable of adjusting the neutron line generated by the neutron generation device to have a preset beam quality, and the neutron line generated by the neutron generation device is irradiated to the irradiated body on the treatment table through the beam shaping body.

A tenth aspect of the invention provides a method for controlling a radioactive ray irradiation system, here, the beam irradiation system includes a beam irradiation device, a treatment plan module and a control module. The beam irradiation device generates a treatment beam and irradiates the treatment beam to an irradiated body, to form an irradiated site. The treatment plan module performs dose simulation and calculation according to parameters of the treatment beam and medical imaging data of the irradiated site and generates a treatment plan. The control module controls irradiation of the beam irradiation device according to the treatment plan. The method for controlling the radioactive ray irradiation system includes the following operations. The treatment plan module performs simulation and calculation by using non-uniform meshes.

The method for controlling the radioactive ray irradiation system may further include the following operations. The treatment plan module sets a size of a mesh of an important area to be less than a size of a mesh of a non-important area.

The method for controlling the radioactive ray irradiation system may further include the following operations. The treatment plan module sets a size of a mesh of an area where a tumor is located to be less than or equal to 0.4 mm.

The method for controlling the radioactive ray irradiation system may further include the following operations. The treatment plan module sets a size of a mesh of an area where each of blood, air and bone is located to be greater than or equal to 1.6 mm, and sets a size of a mesh of an area where a normal muscle is located to be greater than 0.8 mm and less than 1.6 mm.

According to the radioactive ray irradiation system and the method for controlling the radioactive ray irradiation system recited by the embodiments of the invention, simulation and calculation are performed by using non-uniform meshes. Therefore, calculation accuracy of the important area may be improved without significantly increasing calculation time, and the calculation time is reduced in case that calculation accuracy of the non-important area is met.

DETAILED DESCRIPTION

Figure 1:
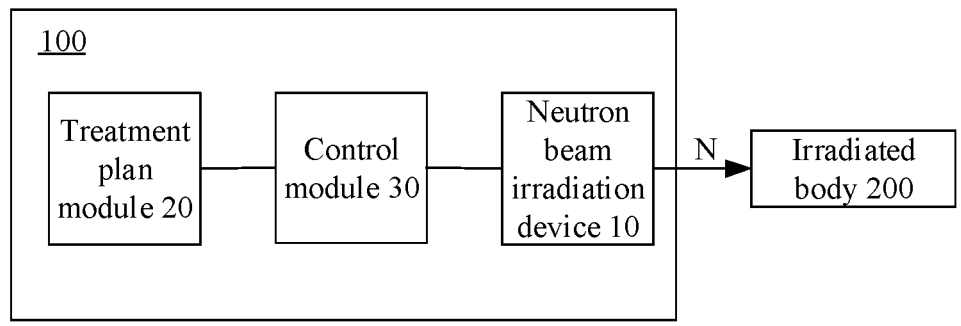
FIG. 1 is a schematic module diagram of a BNCT system according to an embodiment of the invention.

Embodiments of the invention will be further described in detail below with reference to the drawings, to enable those skilled in the art to implement the embodiments with reference to texts of the description.

Application of neutron capture therapy as an effective means for cancer treatment gradually increases in recent years, in which BNCT is most commonly seen, and neutrons supplied to BNCT may be supplied by a nuclear reactor or an accelerator. In BNCT, two heavily charged particles $^4$He and $^7$Li are produced by using a characteristic of a boron ($^{10}$B)-containing drug having a high capture section for a thermal neutron, and through $^{10}$B (n, α) $^7$Li neutron capture and a nuclear fission reaction. The two heavily charged particles have an average energy of about 2.33 MeV, and have characteristics of high linear energy transfer (LET) and short range. LET and range of α particle are 150 KeV/μm and 8 μm respectively, LET and range of the heavily charged particle $^7$Li are 175 KeV/μm and 5 μm respectively, and the two particles have a total range approximately equivalent to a cell size, so that radiation injury to an organism may be limited to a cell level. When the boron-containing drug is selectively aggregated in a tumor cell, a purpose of accurately killing the tumor cell may be achieved on premise of not inducing too large injury to normal tissues, in collocation with a suitable neutron radiation source.

No matter a neutron source of BNCT comes from the nuclear reactor or nuclear reaction of charged particles with a target, a mixed radiation field is generated, that is, a beam contains neutrons and photons from low energy to high energy. For BNCT of a tumor at a deep position, the larger the contents of the rest of irradiation rays except epithermal neutrons, the larger the proportion of non-selective dose deposition in normal tissues, therefore radiation inducing unnecessary dose deposition should be reduced as much as possible. In order to better understand dose distribution of neutrons in a human body, in addition to an air beam quality factor, a human's head tissue prosthesis is used to calculate dose distribution in the embodiments of the invention, and a prosthesis beam quality factor is used as a design reference of a neutron beam.

The International Atomic Energy Agency (IAEA) gives five recommendations to an air beam quality factor of a neutron source used by clinical BNCT. The five recommendations may compare advantages and disadvantages of different neutron sources, and serve as a reference for selecting a neutron generation pathway and designing a beam shaping body. The five recommendations are as follows:

Epithermal neutron flux>1×10$^9$ n/cm$^2$s
Fast neutron contamination<2×10$^{-13}$ Gy–cm$^2$/n
Photon contamination<2×10$^{-13}$ Gy–cm$^2$/n
Thermal to epithermal neutron flux ratio<0.05
Epithermal neutron current to flux ratio>0.7

Note: an epithermal neutron has an energy region between 0.5 eV and 40 KeV, a thermal neutron has an energy region less than 0.5 eV, and a fast neutron has an energy region greater than 40 KeV.

With reference to FIG. 1, the radioactive ray irradiation system in this embodiment is a BNCT system 100, and includes a neutron beam irradiation device 10, a treatment plan module 20 and a control module 30. The neutron beam irradiation device 10 generates a treatment neutron beam N and irradiates the treatment neutron beam N to an irradiated body 200, to form an irradiated site. The treatment plan module 20 performs dose simulation and calculation according to parameters of the treatment neutron beam N generated by the neutron beam irradiation device 10 and medical image data of the irradiated site and generates a treatment plan which determines a position of the irradiated site relative to the neutron beam irradiation device 10 during irradiation treatment and a corresponding irradiation time. After the irradiated body 200 is positioned according to the position determined by the treatment plan, treatment may be started, and the control module 30 retrieves a current treatment plan corresponding to the irradiated body 200 from the treatment plan module 20, and controls irradiation of the neutron beam irradiation device 10 according to the treatment plan. The control module 30 may also receive other data information, such as data of the neutron beam irradiation device 10, data of the irradiated body 200, or the like.

Figure 2:
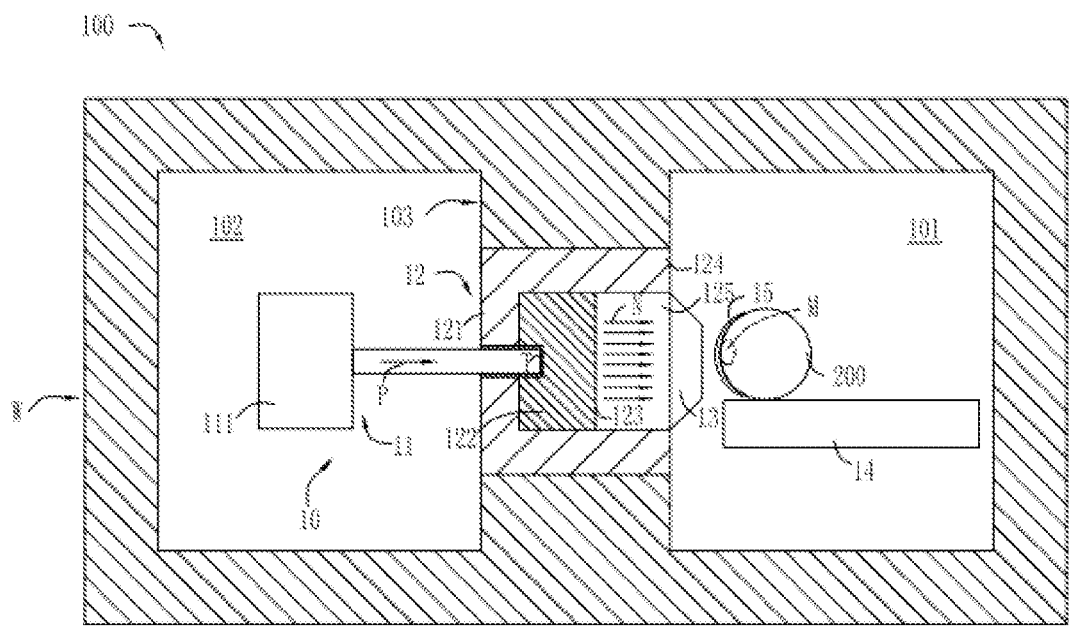
FIG. 2 is a schematic structural diagram of a BNCT system according to an embodiment of the invention.

With reference to FIG. 2, in this embodiment, the neutron beam irradiation device 10 includes a neutron generation device 11, a beam shaping body 12, a collimator 13 and a treatment table 14. The neutron generation device 11 includes an accelerator 111 and a target T, the accelerator 111 accelerates charged particles (such as protons, deuterium cores, or the like) to generate a charged particle line P such as a proton line, the charged particle line P irradiates to the target T and acts with the target T to generate a neutron line (a neutron beam) N. Preferably, the target T is a metal target. An appropriate nuclear reaction may be selected according to characteristics such as a desired neutron yield and energy, available energies of the accelerated charged particles, a current, physical and chemical properties of the metal target, or the like. Nuclear reactions as commonly discussed include $^7$Li(p, n) $^7$Be and $^9$Be(p, n) $^9$B, both of which are endothermic reactions and have energy thresholds of 1.881 MeV and 2.055 MeV respectively. An ideal neutron source for BNCT is an epithermal neutron at a keV energy level, then theoretically, when protons with energies only slightly higher than the threshold are used to bombard a metallic lithium target, neutrons with relatively low energies may be generated for clinical application without too much retarding treatment. However, proton action sections of lithium (Li) and beryllium (Be) metallic targets with the threshold energy are not high, therefore protons with higher energies are usually selected to initiate a nuclear reaction, to generate a large enough neutron flux. An ideal target should have a high neutron yield, the generated neutron energy distribution is close to an epithermal neutron energy region (it will be described in detail below), there is not too much strong penetrating radiation, and there are characteristics such as safe, cheap, easy to operate, resistant to high temperature, or the like. However, nuclear reactions that meet all requirements may not be found actually, and the target made of metal Li is used in the embodiments of the invention. However, it is well known by those skilled in the art that the target T may also be made of a metal material other than Li and Be, for example, the target T may be formed by tantalum (Ta), tungsten (W) or the like. The target T may be in a shape of a circular plate or another solid shape, or may also use a liquid (liquid metal). The accelerator 111 may be a linear accelerator, a cyclotron, a synchrotron, a synchrocyclotron, and the neutron generation device 11 may also be a nuclear reactor without usage of an accelerator and a target. No matter a neutron source of BNCT comes from the nuclear reactor or nuclear reaction of charged particles of the accelerator with the target, a mixed radiation field is generated actually, that is, a beam contains neutrons and photons from low energy to high energy. For BNCT of a tumor at a deep position, the larger the contents of the rest of irradiation rays except epithermal neutrons, the larger the proportion of non-selective dose deposition in normal tissues, therefore radiation inducing unnecessary dose deposition should be reduced as much as possible. Furthermore, for normal tissues of the irradiated body, too many kinds of irradiation rays should be prevented, which also induces unnecessary dose deposition.

The neutron beam N generated by the neutron generation device 11 is irradiated to the irradiated body 200 on the treatment table 14 by passing through the beam shaping body 12 and the collimator 13 sequentially. The beam shaping body 12 is capable of adjusting a beam quality of the neutron beam N generated by the neutron generation device 11, and the collimator 13 converges the neutron beam N, so that the neutron beam N has high targeting performance during treatment. It may be understood that the invention may not have a collimator, and the beam is directly irradiated to the irradiated body 200 on the treatment table 14 after coming out of the beam shaping body 12.

The beam shaping body 12 further includes a reflector 121, a retarder 122, a thermal neutron absorber 123, a radiation shield 124 and a beam outlet 125. Neutrons generated by the neutron generation device 11 have large energy spectrums, contents of other kinds of neutrons and photons are required to be reduced as much as possible, except epithermal neutrons meeting treatment requirements, to avoid injuries to an operator or the irradiated body. Therefore, neutrons emitted from the neutron generation device 10 are required to pass through the retarder 22 to adjust a fast neutron energy (>40 keV) thereof to the epithermal neutron energy region (0.5 eV to 40 keV) and reduce thermal neutrons (<0.5 eV) as much as possible. The retarder 22 is made of a material having a large cross-section acting with fast neutrons and a small cross-section acting with epithermal neutrons. As a preferred embodiment, the retarder 122 is made of at least one of $D_2O$, $AlF_3$, Fluenal™, $CaF_2$, $Li_2CO_{23}$, $MgF_2$, or $Al_2O_3$. The reflector 121 surrounds the retarder 122, and reflects neutrons diffused around by passing through the retarder 122 back to the neutron beam N to improve utilization rate of neutrons, and is made of a material having a strong neutron reflection capability. As a preferred embodiment, the reflector 121 is made of at least one of Pb or Ni, the thermal neutron absorber 123 is arranged at the rear of the retarder 122 and made of a material having a large cross-section acting with thermal neutrons. As a preferred embodiment, the thermal neutron absorber 123 is made of Li-6, and the thermal neutron absorber 123 absorbs thermal neutrons passing through the retarder 122 to reduce contents of thermal neutrons in the neutron beam N, avoiding excessive dose induced on normal tissues at shallow layers during treatment. It may be understood that the thermal neutron absorber may also be integrated with the retarder, and a material of the retarder contains Li-6. The radiation shield 124 shields neutrons and photons leaked from positions outside of the beam outlet 125, and a material of the radiation shield 124 includes at least one of a photon shielding material or a neutron shielding material. As a preferred embodiment, the material of the radiation shield 124 includes lead (Pb) used as the photon shielding material and polyethylene (PE) used as the neutron shielding material. The collimator 13 is arranged at the rear of the beam outlet 125, and an epithermal neutron beam coming out of the collimator 13 is irradiated to the irradiated body 200, and after passing through the normal tissues at shallow layers, the epithermal neutron beam is slowed down to thermal neutrons to reach a tumor cell M. It may be understood that the beam shaping body 20 may also have other configurations, as long as the epithermal neutron beam required for treatment may be obtained. For ease of description, when the collimator 13 is provided, an outlet of the collimator 13 may also be used as the beam outlet 125 as described below. In this embodiment, a radiation shielding device 15 is further arranged between the irradiated body 200 and the beam outlet 125 to shield irradiation of a beam coming out of the beam outlet 125 to the normal tissues of the irradiated body, and it may be understood that the radiation shielding device 15 may not be provided.

After a boron (B-10)-containing drug is taken by or injected to the irradiated body 200, the boron-containing drug is selectively aggregated in the tumor cell M, and then two heavily charged particles $^4$He and $^7$Li are generated by using a characteristic of the boron (B-10)-containing drug having a high capture section for a thermal neutron, and through $^{10}$B (n, α) $^7$Li neutron capture and a nuclear fission reaction. The two charged particles have an average energy of about 2.33 MeV, and have characteristics of high LET and short range. LET and range of α particle are 150 keV/μm and 8 μm respectively, LET and range of the heavily charged particle $^7$Li are 175 keV/μm and 5 μm respectively, and the two particles have a total range approximately equivalent to a cell size, so that radiation injury to an organism may be limited to a cell level, and a purpose of locally killing tumor cells may be achieved on premise of not inducing too large injury to normal tissues.

The BNCT system 100 is integrally contained in a building of concrete structure. In particular, the BNCT system 100 further includes an irradiation chamber 101 and a charged particle beam generation chamber 102. The irradiated body 200 on the treatment table 14 is subjected to irradiation treatment of the neutron beam N in the irradiation chamber 101. The charged particle beam generation chamber 102 at least partially contains the accelerator 111, and the beam shaping body 12 is at least partially contained in a partition wall 103 between the irradiation chamber 101 and the charged particle beam generation chamber 102. It may be understood that the partition wall 103 may completely separate the irradiation chamber 101 from the charged particle beam generation chamber 102; or may be a partial separation between the irradiation chamber 101 and the charged particle beam generation chamber 102, so that the irradiation chamber 101 is in communication with the charged particle beam generation chamber 102. There may be one or more targets T, the charged particle line P may selectively act with one or more targets T or simultaneously act with a plurality of targets T to generate one or more treatment neutron beams N. Corresponding to the number of targets T, there may also be one or more beam shaping bodies 12, collimators 13 and treatment tables 14; a plurality of treatment tables may be arranged in the same irradiation chamber, or a separate irradiation chamber may be provided for each treatment table. The irradiation chamber 101 and the charged particle beam generation chamber 102 are spaces formed by surrounding of a concrete wall W (including the partition wall 103), and the concrete structure may shield neutrons and other irradiation rays leaked in an operation process of the BNCT system 100.

In order to kill cancer cells to the maximum extent while reducing injury to normal tissues induced by the irradiation rays, accuracy of dose distributions of epithermal neutrons and photons are particularly important in setting of the treatment plan module 20. In application scenes of the radioactive ray irradiation system, dose calculation needs to read photon and neutron cross-section databases, here, the neutron cross-section database is very huge, resulting in occupation of a large storage space when a software for formulating a treatment plan of the radioactive ray irradiation system is installed, and a large memory space is occupied and calculation time is long when the software is used for dose calculation and simulation. In the following embodiments of the invention, a series of methods for optimizing the treatment plan module are provided, so that time for dose calculation is reduced while a running memory is reduced, to meet requirements of quickly formulating a radiotherapy plan scheme. Each optimization method is described below with reference to the drawings.

First embodiment: optimization of database in the treatment plan module 20.

There are more than 60 elements in total within the human body, here, there are more than 20 elements which are essential elements and are of great significance to maintain normal physiological functions of the body. Elements with large contents in the human body are carbon, hydrogen, oxygen, nitrogen, phosphorus, chlorine, sodium, magnesium, potassium, calcium, or the like, here, carbon, hydrogen, oxygen and nitrogen are main elements constituting organic matters of the human body and account for 96% of a total weight of the human body, and the rest macroelements greater than 0.01% of the human body are calcium, potassium, phosphorus, sulfur, chlorine, magnesium and sodium respectively, which account for 1.5%, 0.35%, 1%, 0.25%, 0.15%, 0.05% and 0.15% of the total weight of the human body respectively. It may be seen that contents of carbon, hydrogen, oxygen, nitrogen, calcium, potassium, phosphorus, sulfur, chlorine, magnesium and sodium has reached 99.45% of the total weight of the human body. Furthermore, Monte Carlo stores simulation and calculation systems of more than 100 elements, and each time Monte Carlo is used for simulation and calculation, each element is simulated and calculated, which consumes a long time. Furthermore, since calculation and simulation systems corresponding to many elements are stored, a Monte Carlo database is very huge. However, in the application scenes of the radioactive ray irradiation system, when particles such as photons, neutrons, or the like in the human body are simulated and calculated by Monte Carlo, only elements in the human body with large proportions (greater than 0.01%) with respect to the total weight of the human body are required to be simulated and calculated, to obtain a relatively accurate calculation result, while simulation and calculation of some trace elements may occupy much time, and when the resulting calculation result is compared with a result obtained by performing simulation and calculation on only the elements occupying 0.01% or more of the total weight of the human body, a difference is less than 0.001%.

Furthermore, certain elements, such as Fe, have a large weight proportion in the human body, but these elements do not react with neutrons and photons or have few intensities of reacting with neutrons and photons, therefore, influence of simulation and calculation results of such elements on an overall calculation result may be ignored. However, some elements, such as boron, have a small weight proportion in the human body, but a large number of boron drugs may be injected into the human body in the application scenes of the radioactive ray irradiation system and have relatively intense reaction with neutrons, and thus have large influence on a final calculation result.

Elements (selected from one or more of H, He, Li, Be, B, C, N, O, F, Na, Mg, Al, Si, P, S, Cl, Ar, K and Ca) with influence on simulation and calculation results of neutrons and photons in the application scenes of the radioactive ray irradiation system are screened by considering weight proportions of elements in the human body and intensities of the elements reacting with the neutrons and the photons, so that only the screened elements are simulated during simulation. Therefore, simulation and calculation time is reduced on premise of ensuring calculation accuracy, thereby improving Monte Carlo operation efficiency. Furthermore, database capacities corresponding to the screened elements is only 2% to 3% of an original database capacity, which greatly reduces memory requirement of a disk and reduces manufacturing cost.

On the other hand, in a neutron cross-section database corresponding to each element, cross-section data of a plurality of temperatures are stored in a Monte Carlo system for selection, such as 0 K, 1200 K, 2500 K, 250 K, 294 K, 600 K, 900 K, but in the application scenes of the radioactive ray irradiation system, only a human body model needs to be simulated and calculated, and a normal temperature of the human body is between 310 K and 315 K. According to a Monte Carlo operation principle, after temperature is input, the system automatically matches a temperature closest to the input temperature among a plurality of stored temperatures and performs simulation and calculation by taking the temperature as a simulation parameter. Therefore, after the temperature of the human body is input, the system automatically matches a temperature 294 K stored in the database, and performs simulation and calculation by taking 294 K as a parameter. Furthermore, during calculation of Doppler effect, a temperature of 0 K is used. That is to say, in the application scenes of the radioactive ray irradiation system, only two temperatures of 294 K and 0 K among the temperatures stored in the database are used, and the rest of temperatures are redundant to application of the radioactive ray irradiation system. Therefore, databases corresponding to other temperatures except 294 K and 0 K are removed, and a size of the database may be reduced to about one third of an original size without affecting a simulation and calculation structure, thereby reducing operation cost of the database.

In table 1, there is shown a result of the Monte Carlo system performing neutron dose simulation and calculation on the same human body model at temperatures of 294 K, 310 K and 330 K respectively.

TABLE 1

Result of the Monte Carlo system performing neutron dose simulation and calculation on the same human body model at temperatures of 294 K, 310 K and 330 K

| Temperature | 294 K | 310 K | 330 K |
|---|---|---|---|
| Neutron dose | 146.63 eV/g | 146.085 eV/g | 145.596 eV/g |

It may be seen from data of table 1 that influence of a small-range fluctuation of the temperature on a final calculation result of the neutron dose may be ignored, and in the application of the radioactive ray irradiation system, only the database corresponding to 294 K and stored in the system is retained, which may meet usage requirements, and an error generated by the final calculation result is within an acceptable range.

Second embodiment: interrupting process during particle simulation to reduce particle simulation time.

In the application scenes of the radioactive ray irradiation system, dose calculation includes neutron dose calculation and photon dose calculation. During movement of photons in a to-be-irradiated body, energy and semi-absorption thickness of the photon are gradually reduced, and an absorption cross-section of the photon quickly increases with reduction of the energy and semi-absorption thickness of the photon. When the semi-absorption thickness of the photon is less than a cell size, the photon is absorbed in a cell where the photon is located with a very big probability, and at this time, the photon is directly set to deposit all energy thereof in the cell where the photon is located, and simulation of the photon is no longer continued. An error between this process and dose distribution calculated by continuing simulation of the photon is within 0.1%.

A human cell has a size of 2 to 200 microns, and generally, in the application of the radioactive ray irradiation system, a mesh of a model has a minimum size of 0.8 mm, therefore, simulation of the photon may be stopped when the semi-absorption thickness of the photon is less than a quarter of the minimum mesh size.

Specifically, the semi-absorption thickness t of the photon is calculated by a formula (1-1):

$$t = \frac{\ln 2}{\mu} \approx \frac{0.693}{\mu} \qquad (1\text{-}1)$$

here μ is a linear attenuation factor of the photon which is determined by a material passed by the photon and photon energy.

Semi-absorption thicknesses of different photon energy values in a human skeleton are calculated below by taking the human skeleton as an example.

TABLE 2 semi-absorption thicknesses of different photon energies in a skeleton

| Photon energy | Semi-absorption thickness (mm) |
| --- | --- |
| 0.1 | 0.0006 |
| 1 | 0.001 |
| 4 | 0.029 |
| 6 | 0.089 |
| 8 | 0.105 |
| 10 | 0.137 |
| 12 | 0.365 |
| 14 | 0.471 |
| 16 | 0.586 |
| 18 | 0.867 |
| 20 | 0.970 |

It may be seen from table 2 that in the skeleton, the semi-absorption thickness of the photons is less than 0.2 mm when the photon energy is less than 10 KeV, that is, when the photon energy is less than 10 KeV, the photon may be absorbed in a mesh where the photon is located currently with a very big possibility, and therefore, a difference between dose obtained by stopping simulation of the photon at this time and dose obtained by further simulating the photon is within an acceptable range.

Since a semi-absorption thickness of the photon in a cell tissue depends on a material passed by the photon and photon energy, a corresponding interruption energy may be provided for each material, and simulation of the photon may be stopped when the photon energy is lower than the interruption energy. Photon dose corresponding to different photon interruption energies are obtained by performing simulation and calculation in the human body model below.

TABLE 3 photon energies obtained by performing simulation and calculation through setting different photon interruption energies in the human body model

| Photon interruption energy (KeV) | Photon dose (eV/g) |
| --- | --- |
| 0.1 | 3.00831 |
| 1 | 3.00850 |
| 4 | 3.00905 |
| 6 | 3.01007 |
| 8 | 3.01009 |
| 10 | 3.01101 |
| 12 | 3.01302 |
| 15 | 3.01305 |
| 18 | 3.01309 |
| 20 | 3.01501 |

It may be seen from table 2 that simulation of the photon is stopped when the photon energy is less than or equal to 10 KeV, and an error between a finally calculated photon dose and dose distribution calculated by continuing simulation of the photon is within 0.1%.

In conclusion, during simulation and calculation of the photon, the semi-absorption thickness of the photon is less than a cell size when the photon energy is less than a preset interruption energy, and at this time, simulation of the photon is stopped, which may reduce a photon dose calculation time without affecting a dose distribution calculation result.

In other embodiments, a first preset value and a second preset value may be set according to actual simulation accuracy requirements, simulation of a photon is stopped in response to a semi-absorption thickness of the photon being less than or equal to the first preset value, or in response to the photon energy being less than or equal to the second preset value. The first preset value may be greater than a cell size, or may be less than a cell size, and the second preset value may be 12 KeV, 16 KeV, or the like.

Third embodiment: accelerating a dose calculation module by using a parallel technology.

Monte Carlo method is used in the treatment plan module of the radioactive ray irradiation system, simulation processes of different source particles are completely independent, that is to say, simulation sequences of different particles have no influence on a calculation result. According to such calculation characteristics, simulation tasks of different source particles may be allocated to different processes or threads, and summarization is performed after a calculation task of each of the processes or threads is completed, to obtain a final calculation result. A computer may provide two forms of parallelism: process parallelism and thread parallelism of CPU, and GPU acceleration.

Figure 3:
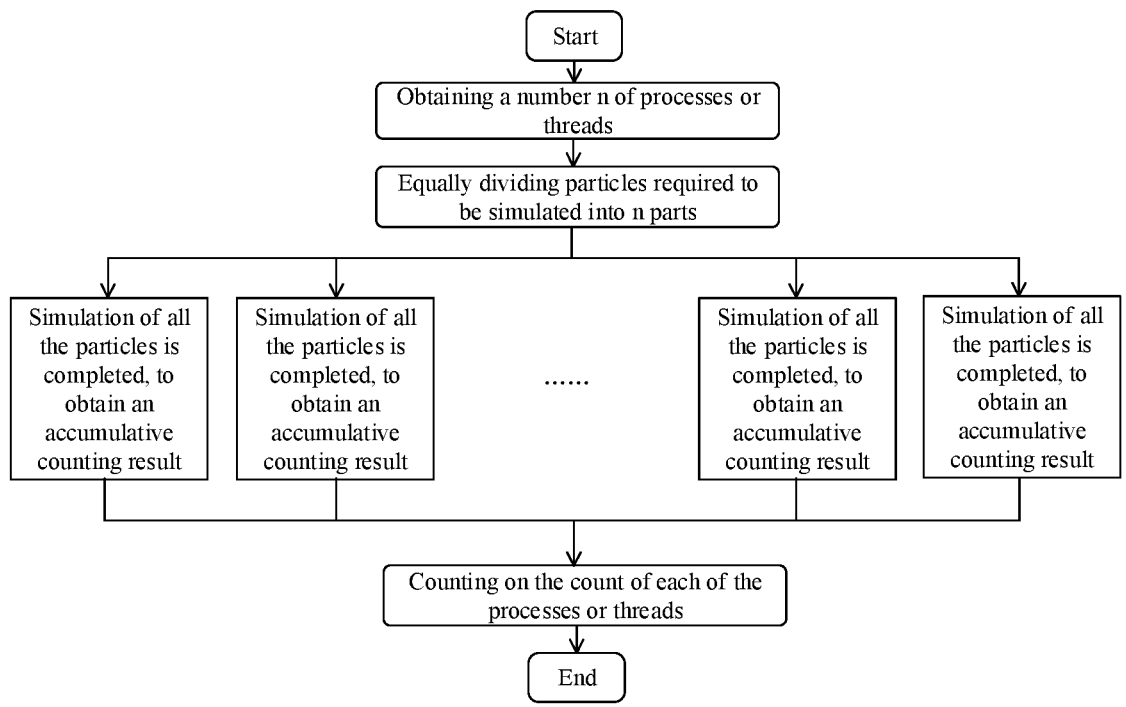
FIG. 3 is a computation flowchart of process parallelism and thread parallelism of CPU according to an embodiment of the invention.

With reference to FIG. 3, a calculation process of the process parallelism and thread parallelism of the CPU is as follows. Firstly, the system obtains a number of processes or threads to obtain a numerical value n; then, the system equally divides particles required to be simulated into n parts; next, each of the threads or processes separately simulates and counts each part of the particles; and finally, the system performs counting on the count obtained by each of the processes or threads to obtain a final dose. Since the particles are allocated to different processes or threads so as to perform simulation and calculation simultaneously, time of simulation and calculation is shortened to 1/n (process) or 1/2n of time required to use one thread or process to simulate and calculate all the particles.

Each of the process parallelism and the thread parallelism implements parallel computation by a multi-core CPU, and the GPU acceleration is implemented by parallel computation of a plurality of processors of GPU. Effect of each of the process parallelism and the thread parallelism is limited to a number of cores of CPU, the number of cores of a common stand-alone computer is four, the process parallelism and the thread parallelism may increase speed by 4 times (process) or 8 times (thread) at most, and one GPU integrates a plurality of processors, and theoretically, calculation speed may be increased by a plurality of times.

Figure 4:
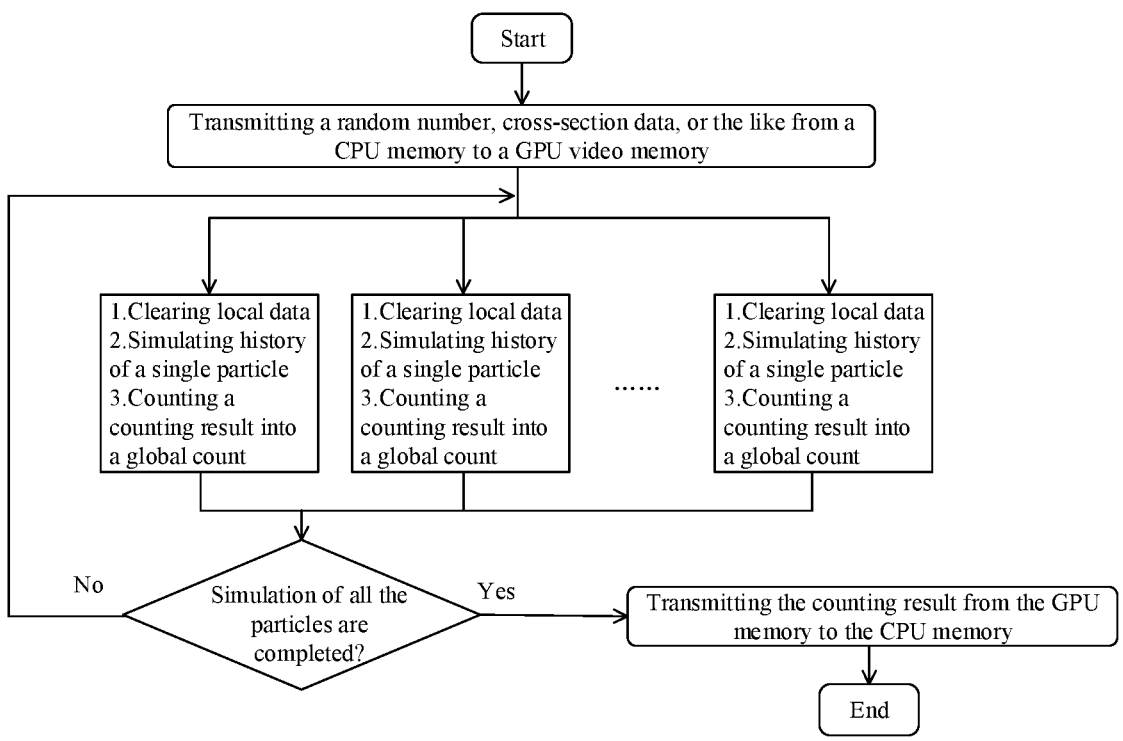
FIG. 4 is a flowchart of simulation and computation of GPU acceleration according to an embodiment of the invention.

With reference to FIG. 4, a simulation and computation process of the GPU acceleration is as follows. Firstly, the system transmits a random number, cross-section data, or the like from a CPU memory to a GPU video memory, and then each of the plurality of processors of the GPU simulates, calculates and counts a single particle, and counts a counting result into a global count; next, the system determines whether there are particles which are still not simulated, transmits the counting result from the GPU memory to the CPU memory in response to no particles which are still not simulated, or returns to the previous operation in response to particles which are still not simulated, to continue to simulate and count the particles which are still not simulated, until simulation of all the particles are completed.

Since GPU has a plurality of processors, simulation and computation with the GPU acceleration may greatly increase calculation speed and reduce calculation time. Furthermore, CPU uses Intel Xeon Processor with 2.27 GHz with a price of about 6000 RMB, GPU uses NVIDIA Tesla C2050 with a price of about 9000 RMB, and each GPU has a total of 448 processors equivalent to 448 CPUs. Calculation time of CPU is 50 to 70 times of calculation time of GPU. It may be seen that compared with CPU, GPU is used to perform simulation and calculation, which has great advantages in both price and time consumption.

Fourth embodiment: using Monte Carlo variance reduction skill to accelerate convergence.

Monte Carlo method has rich variance reduction skills to increase calculation speed of a program, here, variance reduction skills which may be used by the treatment plan system include implicit capture, a weight window game, betting for split, or the like. Here, betting for split is composed of a betting skill and a splitting skill. The betting skill, the splitting skill, mesh space importance, implicit capture and the weight window game involved in the variance reduction skill are explained below.

Betting skill: in general, the weight of the particle has an upper limit of 10 and a lower limit of 0.25. When the weight w of the particle is reduced to be less than a certain preset value (e.g., 0.25), a random number x is sampled between 0 and 1, and when x is less than w, the particle is survive and the weight of the particle is returned to 1; when x is greater than or equal to w, there is dead betting for the particle, and simulation of the particle is terminated.

Splitting skill: when the weight w of the particle is greater than a certain value (e.g., 10), an integer part of w is set to be w1, a decimal part of w is set to be w2, a random number x is sampled between 0 and 1, w=w1+1 is set when x is less than w2, and w=w1 is set when x is greater than w2. Then, a particle is split into w particles for simulation, until weight of each of the particles is reduced to 1.

Mesh space importance: particles at different areas of a model have different contributions to dose, contribution of the particle to the dose is characterized by space importance, and mesh space importance of each mesh is calculated according to parameters such as a tumor position, model characteristics, or the like, before simulation. The particle moves from a mesh with mesh space importance of $I_n$ to a mesh with mesh space importance of $I_{n+1}$, and when $I_{n+1} > I_n$, $m = I_{n+1}/I_n$ is set, the particle is split into m particles, weight of each of the particles is reduced to 1/m of an original weight; when $I_{n+1} < I_n$, a betting skill is performed on the particle, $P = I_{n+1}/I_n$ is set, a random number x is sampled between 0 and 1, and when x is less than P, the particle is survive and the weight is multiplied with 1/P, otherwise, there is dead betting for the particle, and simulation of the particle is terminated.

Method for calculating the mesh space importance: the mesh space importance may be obtained by calculating an accompanying flux obtained by solving an accompanying transportation equation which has a form as follows:

$$-\frac{1}{v}\frac{\partial \phi^*(r, E, \Omega, t)}{\partial t} - \Omega \cdot \nabla \phi^*(r, E, \Omega, t) + \Sigma_t(r, E)\phi^*(r, E, \Omega, t) =$$
$$S^*(r, E, \Omega, t) + \int\int \Sigma_s(r, E \to E', \Omega \to \Omega')\phi^*(r, E', \Omega', t)d\Omega', dEdE'$$

here φ* is an accompanying flux, S* is an accompanying source, v is a movement velocity of the particle, Ω is a movement direction of the particle, $\Sigma_t$ is a reaction cross-section of the particle colliding with a substance, $\Sigma_s$ is a scattering cross-section, r is position of the particle, E is energy of the particle, and t is time.

Implicit capture: when the particle interacts with the substance, the particle is scattered only and is not absorbed, and the weight of the particle is multiplied with $P_{scattering}/P_{total}$ in each collision. When the weight of the particle is reduced to a certain value (e.g., 0.25), the particle are processed by using a betting skill.

Weight window game: when the weight of the particle is greater than a certain value, such as 10, a splitting skill is performed, and when the weight of the particle is less than a certain value, such as 0.25, a betting skill is performed. Here, the two values are set according to software performance.

In general, when the particle moves from a place with small mesh space importance to a place with large mesh space importance, the weight of the particle is increased, and there is not dead betting for the particle; and a case where the weight is reduced means that when the particle moves from a place with large mesh space importance to a place with small mesh space importance, the weight of the particle is reduced, the particle is split or implicitly captured. Since a thermal neutron has a large absorption cross-section in the human body (mainly elements such as N, B, or the like), in order to accelerate convergence speeds of dose calculation of meshes far away from the neutron source, implicit capture should be used to move the particle into the meshes. When the particle is far away from a treatment area, continuing to simulate dose calculation of the particle on the treatment area is not of great significance, and at this time, waste of calculation resources may be induced by continuing calculation, so that a probability of occurrence of this situation may be reduced by setting the mesh space importance. When the weight of the particle is too small, contribution of the particle to the count is very small, waste of calculation resources is induced by continuing simulation, and when the weight of the particle is too large, a single count is too large, resulting in a risk of result distortion, and thus a weight window should be provided so that the weight of the particle is in a suitable range. Therefore, it is necessary to combine the implicit capture, reasonable setting of the mesh space importance and the weight window game, to accelerate a convergence speed of Monte Carlo program.

Figure 5:
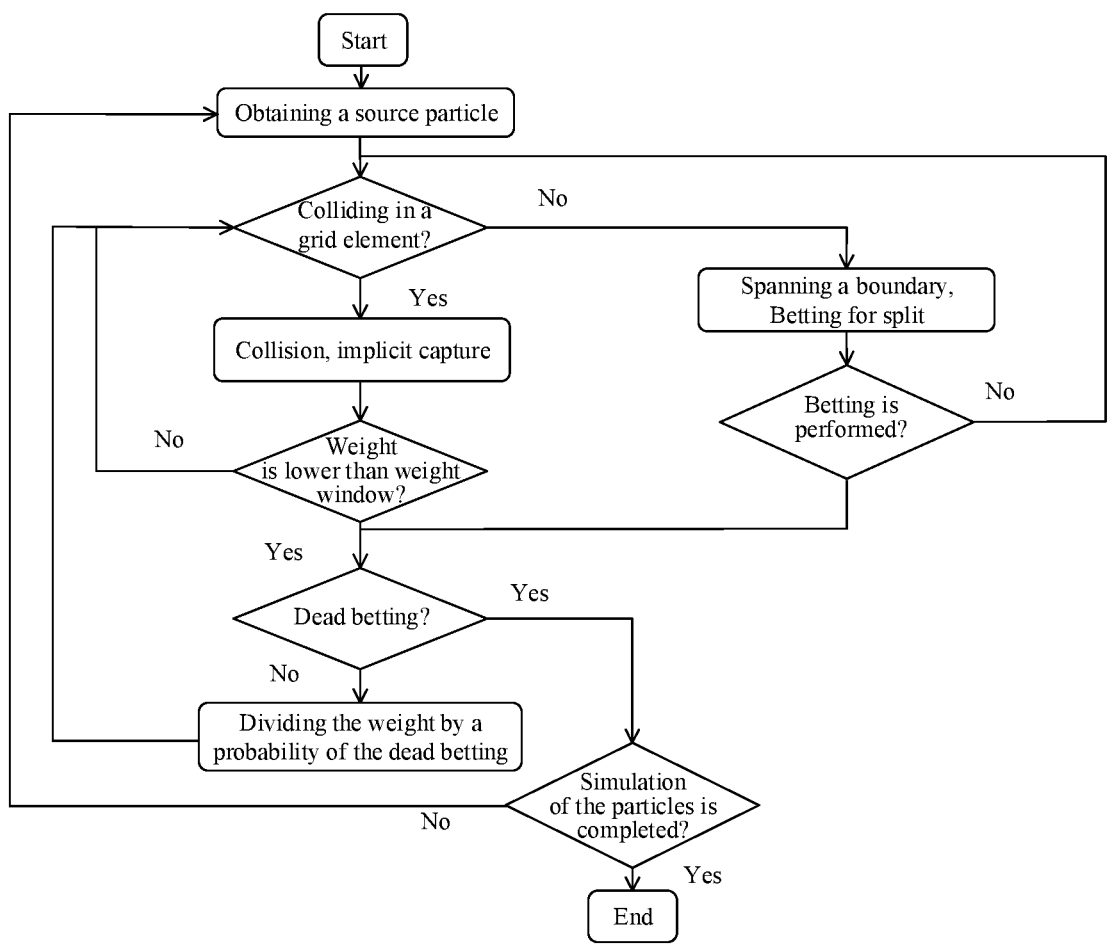
FIG. 5 is a flowchart of simulating particles by using a variance reduction skill according to an embodiment of the invention.

With reference to FIG. 5, a process of simulating the particles by using the variance reduction skill is as follows. In operation S1, a source particle is obtained. In operation S2, it is determined whether the particle collides in a grid element, and operations S3 and S4 are sequentially executed in case of collision, otherwise, operations S5 and S6 are sequentially executed. In operation S3, implicit capture is performed. In operation S4, it is determined whether a weight is lower than a weight window, and operation S7 is executed in response to the weight being lower than the weight window, otherwise, the process returns to operation S2. In operation S5, betting for split is performed. In operation S6, it is determining whether betting is performed, and operation S7 is executed in response to performing the betting, otherwise, the process returns to operation S2. In operation S7, it is determined whether there is dead betting, and operation S8 is executed in response to there being dead betting, otherwise, operation S9 is executed and then the process returns to operation S2. In operation S8, it is determined whether processing of the particles is completed, and the process ends in response to processing of the particles being completed, otherwise, the process returns to operation S1. In operation S9, the weight is divided by a probability of the dead betting.

Figure 6:
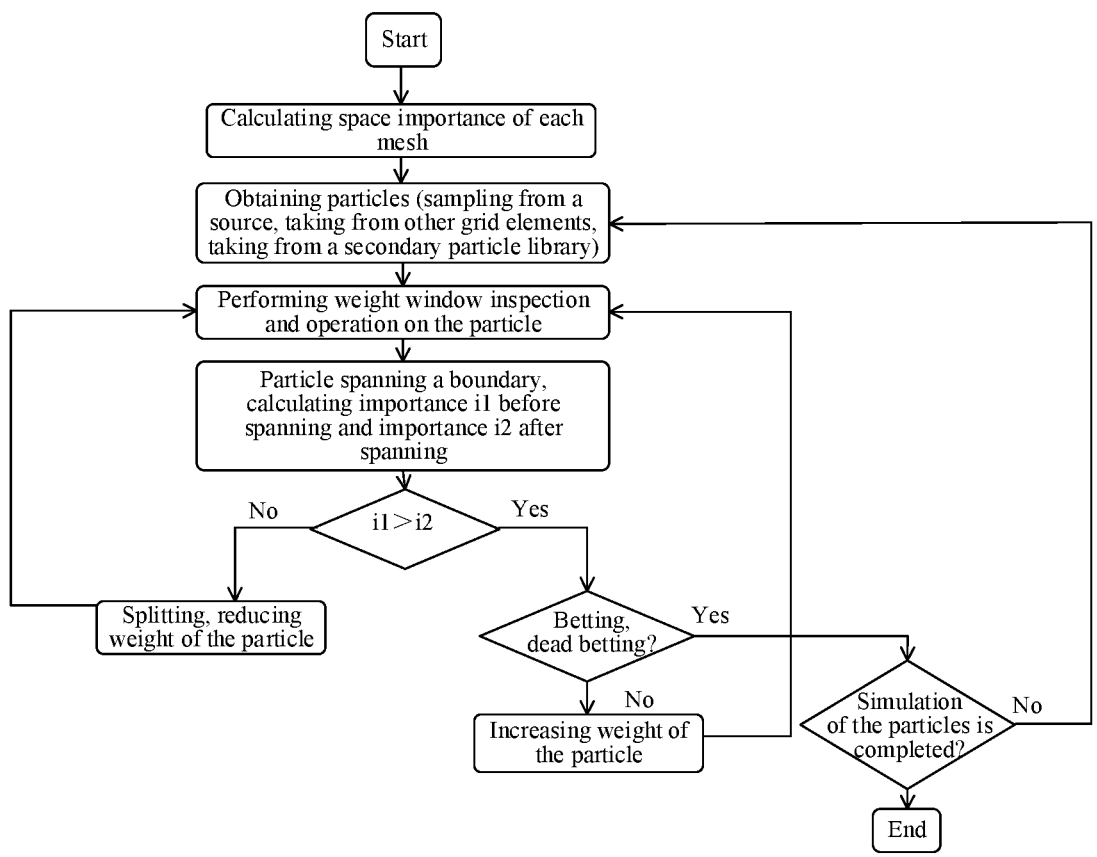
FIG. 6 is a flowchart of betting for split according to an embodiment of the invention.

With reference to FIG. 6, a process of betting for split is as follows. In operation S1, mesh space importance of each mesh is calculated and recorded. In operation S2, particles are obtained. In operation S3, weight window inspection and operation are performed on the particle. In operation S4, mesh space importance $I_n$ and $I_{n+1}$ before and after the particle spans a boundary of the mesh are calculated. In operation S5, comparison is performed to determine whether $I_n$ is greater than $I_{n+1}$, and operation S6 is executed and then the process returns to operation S3 in response to $I_n$ being not greater than $I_{n+1}$, otherwise, operation S7 is executed. In operation S6, the particle is split and weight of the particle is reduced. In operation S7, it is determined whether there is dead betting for the particle, and operation S9 is executed in response to determining that there is dead betting for the particle, otherwise, operation S8 is executed and then the process returns to operation S3. In operation S8, the weight of the particle is increased. In operation S9, it is determined whether simulation of the particles is completed, and the process returns to operation S2 in response to determining that simulation of the particles is not completed, otherwise, the process ends.

Figure 7:
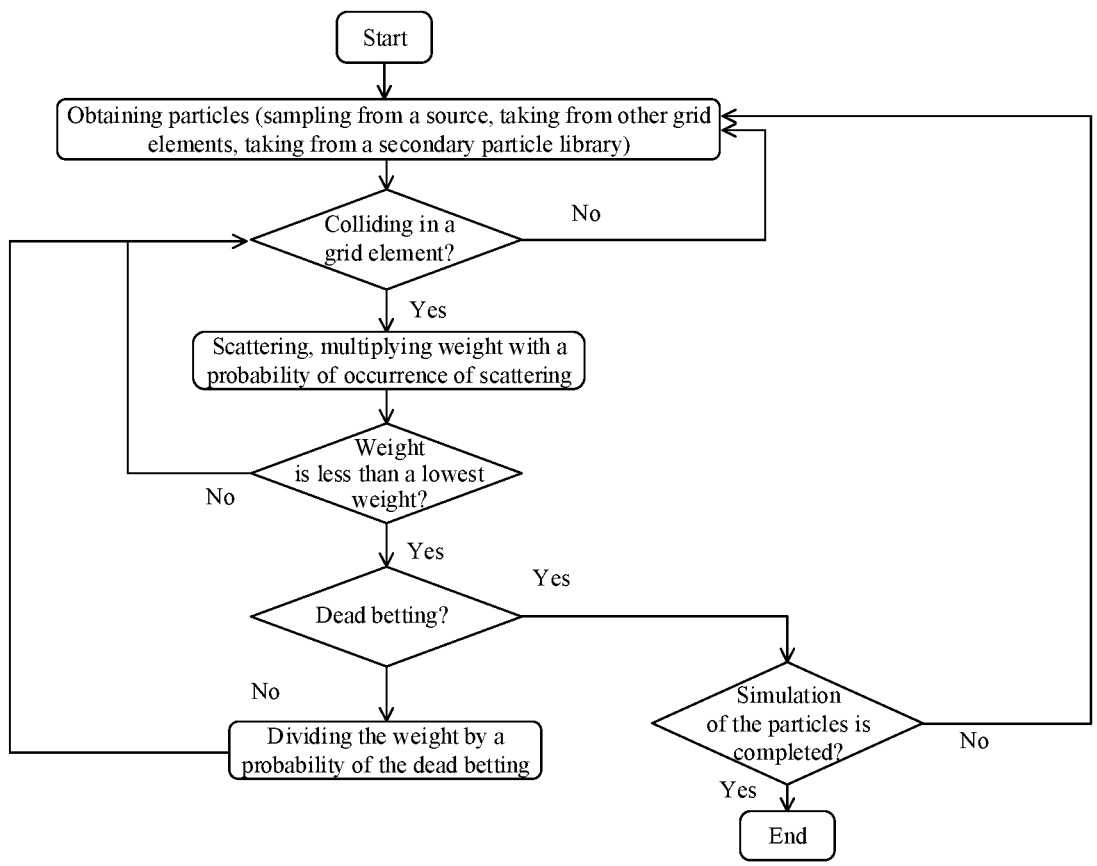
FIG. 7 is a flowchart of implicit capture according to an embodiment of the invention.

With reference to FIG. 7, a process of the implicit capture is as follows. In operation S1, particles are obtained. In operation S2, it is determined whether the particle collides in a grid element, and operation S3 is executed in case of collision, otherwise, the process returns to operation S1. In operation S3, a weight is multiplied with a probability of occurrence of scattering. In operation S4, it is determined whether the weight of the particle is less than a lowest weight, and operation S5 is executed in response to the weight being less than the lowest weight, otherwise, the process returns to operation S2. In operation S5, it is determined whether there is dead betting for the particle, and operation S7 is executed in response to there being dead betting for the particle, otherwise, operation S6 is executed and then the process returns to operation S2. In operation S6, the weight is divided by a probability of the dead betting. In operation S7, it is determined whether simulation of the particles is completed, and the process returns to operation S1 in response to determining that simulation of the particles is not completed, otherwise, the process ends.

Figure 8:
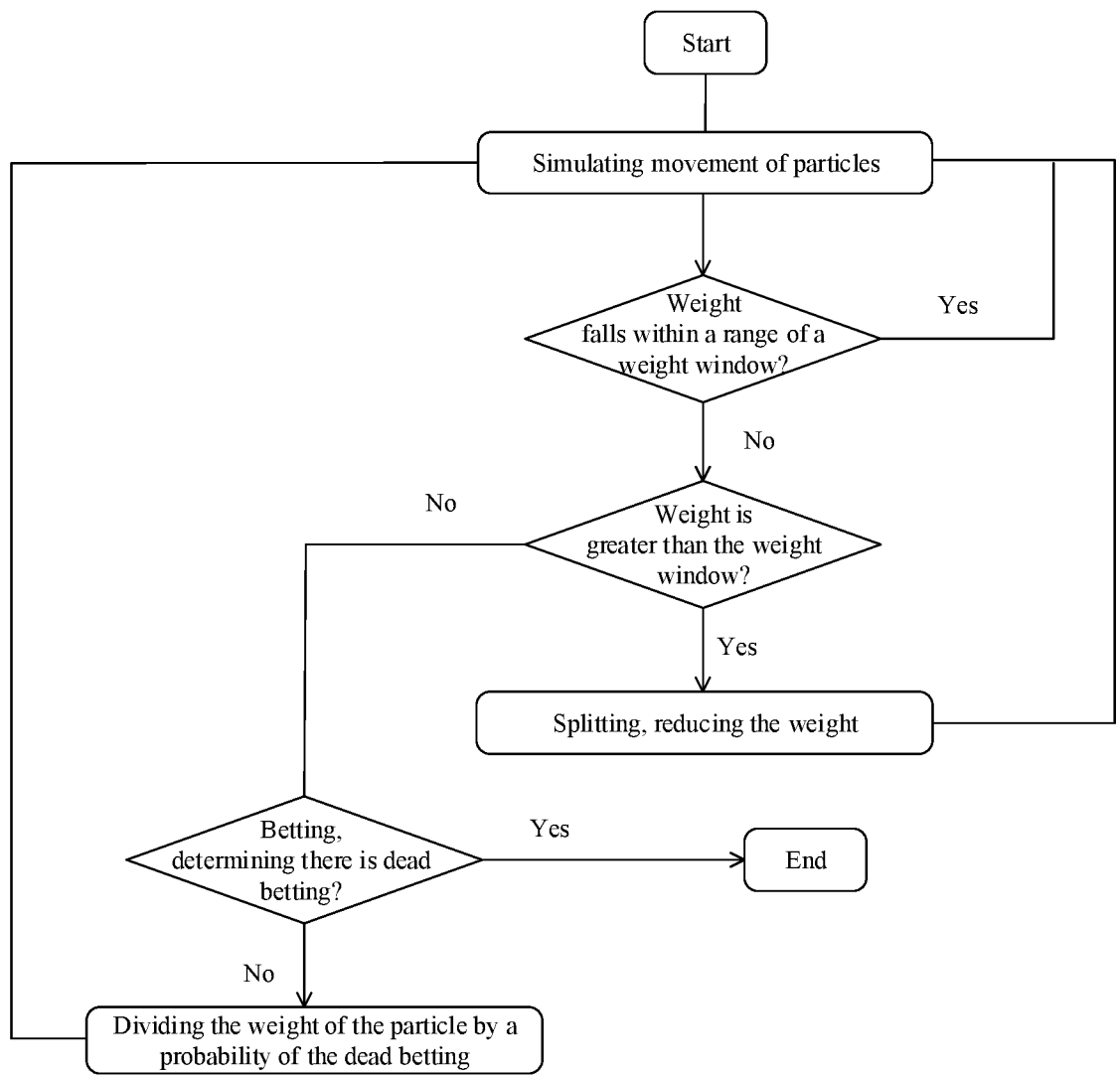
FIG. 8 is a flowchart of a weight window game according to an embodiment of the invention.

With reference to FIG. 8, a process of the weight window game is as follows. In operation S1, movement of the particles is simulated. In operation S2, it is determined whether the weight of the particle falls within a range of a weight window, and the process returns to operation S1 in response to the weight of the particle falling within the range of the weight window, otherwise, operation S3 is executed. In operation S3, it is determined whether the weight is greater than the weight window, operation S4 is executed and then the process returns to operation S1 in response to the weight being greater than the weight window, otherwise, operation S5 is executed. In operation S4, the particle is split and the weight is reduced. In operation S5, it is determined whether there is dead betting, and the process ends in response to there being dead betting, otherwise, operation S6 is executed and then the process returns to operation S1. In operation S6, the weight of the particle is increased.

In order to compare acceleration effects of the variance reduction skill bringing to dose calculation, standard deviations of results and computation time in case of using implicit capture and not using implicit capture is compared. For the same individual membrane model, ten millions of particles are calculated, computation time is 1584 s and a standard deviation of dose calculation is 11% with usage of the implicit capture skill, while computation time is 1258 s and a standard deviation of dose calculation is 14.5% without usage of the implicit capture skill. In order to reduce the standard deviation to the same level as usage of the implicit capture, it is necessary to increase a number of simulated particles to 16 million, and increase simulation and calculation time to 2045 s, which increases calculation time by 461 s compared with usage of the implicit capture skill, that is, usage of the implicit capture skill reduces calculation time by about 20%.

Fifth embodiment: performing simulation and calculation by using non-uniform rectangular meshes.

Traditional body membrane calculation usually uses uniform meshes, and sometimes, a number of meshes has to be increased for fine calculation of some areas, so that calculation time is prolonged, and the memory is increased in an exponential order. Usually, uniform meshes are obtained from a model read from CT or PET, here, many connected areas have the same material, such as air, blood, or the like, and some of the areas do not need to accurately calculate meticulous dose distribution, so that a fine mesh may be replaced by a thicker mesh; and for important positions such as tumors or the like, finer meshes need to be divided, to achieve finer calculation. Dose is calculated by using non-uniform meshes, calculation accuracy of the important area may be improved without significantly increasing calculation time, and the calculation time is reduced in case that calculation accuracy of the non-important area is met.

Meshes of different sizes are set to perform simulation and calculation below, and influence of different mesh sizes on simulation time and calculation accuracy is compared.

TABLE 3 simulation time and calculation accuracy corresponding to meshes with different sizes

| Sizes of meshes | Number of meshes | Required memory/Mb | Computation time/h | Neutron error | Photon error |
|---|---|---|---|---|---|
| 1.6 mm | 650000 | 96 | 4.2 | 3% | 5% |
| 0.8 mm | 2540000 | 360 | 8 | 8% | 0.6% |
| 0.4 mm | 11300000 | 2120 | 15 | 15% | 0 |
| Mixed mesh | 4600000 | 730 | 5.2 | 0.1% | 0.2% |

In this experiment, the mixed mesh used is composed of meshes of 0.4 mm occupying first 5 cm in a neutron incidence direction, meshes of 0.8 mm occupying middle 5 cm in the neutron incidence direction, and meshes of 1.6 mm occupying the rest of the mixed mesh. It may be seen from table 3 that a total number of meshes may be reduced to 2/5 of an original number of meshes of 0.4 mm by using non-uniform meshes, memory required by the meshes is also reduced to 1/3 of an original memory, calculation time is reduced to 34.7% of original calculation time. A result obtained by calculation using meshes of 0.4 mm is taken as a reference, then a result obtained by calculation using mixed meshes has a neutron error less than 0.1% and a photon error less than 0.2%.

Composition of the mixed mesh is not limited to the mode as exemplified above, and may be set according to a specific situation of the to-be-irradiated body. In general, a size of the mesh is determined by a degree of importance of an area, for example, a size of a mesh of an area where a tumor is located is small and is set to be a mesh less than or equal to 0.4 mm, a size of a mesh of an area where each of blood, air and bone is located is relatively large and is set to be greater than or equal to 1.6 mm, and a size of a mesh of an area where another tissue such as a normal muscle or the like is located is set to be greater than 0.8 mm and less than 1.6 mm.

Algorithm used for dose calculation is Monte Carlo algorithm which has an advantage of high calculation accuracy, and disadvantages of low convergence speed and long calculation time, so that optimization of calculation efficiency is the most important part of optimization. According to the optimization method of each of the first to fifth embodiments of the invention, calculation efficiency may be improved with different degrees, and operation time may be reduced.

While the illustrative specific implementations of the invention have been described as above, so that those skilled in the art understand the invention, it should be apparent that the invention is not limited to the scope of the specific implementations, various changes are apparent for those of ordinary skill in the art and fall within the scope of protection of the invention, as long as these changes fall within the spirit and scope of the invention as defined and determined by the appended claims.

We claim:

1. A radioactive ray irradiation system, characterized in that the radioactive ray irradiation system comprises:
a beam irradiation device, generating a treatment beam and irradiating the treatment beam to an irradiated body, to form an irradiated site;
a treatment plan module, performing dose simulation and calculation according to parameters of the treatment beam and medical imaging data of the irradiated site and generating a treatment plan, wherein simulation of a photon is stopped in response to a semi-absorption thickness of the photon being less than or equal to a first preset value; and
a control module, controlling irradiation of the beam irradiation device according to the treatment plan.

2. The radioactive ray irradiation system of claim 1, wherein the radioactive ray irradiation system is a neutron capture therapy system, and the beam irradiation device comprises a neutron generation device, a beam shaping body and a treatment table, the neutron generation device comprises an accelerator and a target, the accelerator accelerates charged particles to generate a charged particle line which acts with the target to generate a neutron line, the beam shaping body is capable of adjusting the neutron line generated by the neutron generation device to have a preset beam quality, and the neutron line generated by the neutron generation device is irradiated to the irradiated body on the treatment table through the beam shaping body.

3. The radioactive ray irradiation system of claim 1, wherein the treatment plan module calculates the semi-absorption thickness t of the photon by a formula (1-1):

$$t = \frac{\ln 2}{\mu} \approx \frac{0.693}{\mu} \qquad (1\text{-}1)$$

where μ is a linear attenuation factor of the photon which is determined by a material passed by the photon and photon energy.

4. The radioactive ray irradiation system of claim 1, wherein the first preset value is a cell size, the first preset value is 0.2 mm, and when photon energy is less than or equal to a second preset value, the semi-absorption thickness of the photon corresponding to the photon energy is less than or equal to the first preset value, wherein the second preset value is 10 KeV.

5. A method for controlling a radioactive ray irradiation system, characterized in that the radioactive ray irradiation system comprises: a beam irradiation device, generating a treatment beam and irradiating the treatment beam to an irradiated body, to form an irradiated site; a treatment plan module, performing dose simulation and calculation according to parameters of the treatment beam and medical imaging data of the irradiated site and generating a treatment plan; and a control module, controlling irradiation of the beam irradiation device according to the treatment plan,
the method for controlling the radioactive ray irradiation system comprises: stopping simulation of a photon, in response to a semi-absorption thickness of the photon being less than or equal to a first preset value.

6. The method for controlling the radioactive ray irradiation system of claim 5, wherein the treatment plan module calculates the semi-absorption thickness t of the photon by a formula (1-1):

$$t = \frac{\ln 2}{\mu} \approx \frac{0.693}{\mu} \qquad (1\text{-}1)$$

where μ is a linear attenuation factor of the photon which is determined by a material passed by the photon and photon energy.

7. The method for controlling the radioactive ray irradiation system of claim 6, wherein the first preset value is a cell size.

8. The method for controlling the radioactive ray irradiation system of claim 6, wherein the first preset value is 0.2 mm.

9. The method for controlling the radioactive ray irradiation system of claim 5, wherein when photon energy is less than or equal to a second preset value, the semi-absorption thickness of the photon corresponding to the photon energy is less than or equal to the first preset value.

10. The method for controlling the radioactive ray irradiation system of claim 9, wherein the second preset value is 10 KeV.

\* \* \* \* \*